United States Patent
Iwata et al.

(10) Patent No.: US 7,169,299 B2
(45) Date of Patent: *Jan. 30, 2007

(54) FRACTIONATING APPARATUS FOR LIQUID CHROMATOGRAPHY

(75) Inventors: Yosuke Iwata, Kyoto (JP); Shuzo Maruyama, Kameoka (JP)

(73) Assignee: Shimadzu Corporation, Kyoto (JP)

( * ) Notice: Subject to any disclaimer, the term of this patent is extended or adjusted under 35 U.S.C. 154(b) by 151 days.

This patent is subject to a terminal disclaimer.

(21) Appl. No.: 10/881,099

(22) Filed: Jun. 29, 2004

(65) Prior Publication Data

US 2005/0006291 A1    Jan. 13, 2005

(30) Foreign Application Priority Data

Jul. 8, 2003    (JP)    ............................. 2003-271990

(51) Int. Cl.
*B01D 15/08*    (2006.01)

(52) U.S. Cl. .................. 210/198.2; 210/656; 210/101; 422/70; 250/288

(58) Field of Classification Search .................. 422/70; 250/288; 436/161, 173; 210/101, 198.2, 210/656

See application file for complete search history.

(56) References Cited

U.S. PATENT DOCUMENTS

| | | | |
|---|---|---|---|
| 4,977,785 A * | 12/1990 | Willoughby et al. ..... | 73/863.12 |
| 5,477,048 A * | 12/1995 | Nakagawa et al. ......... | 250/288 |
| 5,674,388 A * | 10/1997 | Anahara ................. | 210/198.2 |
| 5,690,828 A * | 11/1997 | Clay et al. ................... | 210/634 |
| 6,462,334 B1 * | 10/2002 | Little et al. ................. | 250/281 |
| 6,707,037 B2 * | 3/2004 | Whitehouse ................. | 250/288 |
| 6,709,632 B2 * | 3/2004 | Nakagawa et al. ........... | 422/54 |
| 6,800,849 B2 * | 10/2004 | Staats ........................ | 250/288 |
| 6,803,568 B2 * | 10/2004 | Bousse et al. .............. | 250/288 |
| 6,812,458 B2 * | 11/2004 | Gregori et al. ............. | 250/288 |
| 6,977,369 B2 * | 12/2005 | Yamaguchi et al. ........ | 250/281 |
| 2002/0187073 A1 * | 12/2002 | Moon et al. .................. | 422/70 |
| 2004/0113068 A1 * | 6/2004 | Bousse et al. .............. | 250/288 |
| 2004/0238427 A1 * | 12/2004 | Maruyama et al. ...... | 210/198.2 |
| 2005/0147536 A1 * | 7/2005 | Iwata ......................... | 422/100 |
| 2005/0158215 A1 * | 7/2005 | Iwata et al. ................. | 422/101 |

FOREIGN PATENT DOCUMENTS

| | | |
|---|---|---|
| JP | 2002-156382 | 5/2002 |
| JP | 2004028763 A | 1/2004 |

OTHER PUBLICATIONS

PTO Translation No. 06-2216, Feb. 2006, pp. 1-12.*

* cited by examiner

*Primary Examiner*—Ernest G. Therkorn
(74) *Attorney, Agent, or Firm*—Rankin, Hill, Porter & Clark LLP

(57) ABSTRACT

A distal end portion of a probe has a multi-pipe structure, in which an effluent solution from a high speed liquid chromatography passes through an innermost flow passage, a matrix solution through an outer flow passage, and the air through an outermost flow passage. A distal end of the outermost pipe extends 1.2 mm longer than the distal end of the inner duplex tube to form a liquid reservoir. When dropping a liquid droplet from the distal end of the probe, the air is blown out to expel the liquid gathered in the liquid reservoir to be dropped.

6 Claims, 3 Drawing Sheets

FRACTIONATING APPARATUS FOR LIQUID CHROMATOGRAPHY

BACKGROUND OF THE INVENTION

1. Field of the Invention

The present invention relates to a high speed liquid chromatography, and more particularly to a fractionating apparatus for fractionating an effluent solution from a high speed liquid chromatography by dropping the effluent solution on a micro plate or sample plate.

2. Description of the Related Art

In the field of a proteome analysis for elucidating the structure or action of protein or peptide, MALDI-TOF-MS (matrix assisted laser desorption ionisation time of flight) has been noted recently.

MALDI-TOF-MS is the method for making the mass spectrometry by adding a matrix to a biosample and applying a laser beam thereto to ionize the sample. The amount of sample used here is as small as several µL.

In this case, a pretreatment is performed to prepare the sample in an analyzable state. One of the pretreatment methods involves separating or fractionating peptide employing a high speed liquid chromatography, and adding a matrix solution.

Since the biosample is valuable, and the maximum sample amount for allowing the analysis by MALDI-TOF-MS is as small as several µL, the flow rate range usable for the high speed liquid chromatography is several µL/min or less, or preferably 1 µL/min or less.

In fractionating the effluent solution in the normal flow rate range for the high speed liquid chromatography, a fraction collector with an electromagnetic valve is usually employed because the flow rate is large. However, in the micro high speed liquid chromatography for a minute flow rate range, because the electromagnetic valve can not be employed, a method is taken in which in fractionating and collecting the effluent solution, the probe at the final exit is disposed above an object spot such as MALDI plate or MTP (micro titer plate), the plate is made approach the probe, and the operation waits until the effluent solution makes contact with the plate to stick or drop onto the object spot of the plate.

In the method for waiting until the effluent solution sticks or drops, when the constituent of the effluent solution is the liquid having a large surface tension, the effluent solution is greatly swollen like liquid droplet at the distal end portion of the probe on the exit side and sticks thereto, making it difficult to perform the fine adjustment of the effluent solution to be fractionated on the plate.

SUMMARY OF THE INVENTION

Thus, it is an object of the invention to provide a fractionating apparatus capable of making the fine adjustment for the drop amount of liquid.

This invention provides a fractionating apparatus for fractionating an effluent solution fed from a liquid chromatography, the apparatus comprising:

a probe for dropping the effluent solution from its distal end, the probe having a mixture flow passage for mixing an additive constituent other than the effluent solution into the effluent solution, and a gas exhaust nozzle for blowing a gas to expel a liquid to be desorbed from a distal end of the probe.

In the fractionating apparatus of the invention, the probe may have a multi-pipe structure at its distal end portion, the multi-pipe structure having a central flow passage, an outer flow passage and an outermost flow passage, wherein the effluent solution passes through the central flow passage, the additive constituent passes through the outer flow passage, and the gas passes through the outermost flow passage, and wherein a distal end of an outermost pipe extends beyond a distal end of inner pipes.

Also, a liquid droplet may be accumulated at the distal end of the probe depending on the material of the probe, and if the effluent solution contains a constituent having a large surface tension, the liquid droplet is swollen to reach the surface of the probe, in which there is the possibility that the drop at each spot is not only less uniform but also the contamination of effluent solution constituents is caused. Thus, an outermost surface of the probe maybe coated with a hydrophobic substance.

The additive constituent flowing through the flow passage of the probe may be a matrix solution for MALDI-TOF-MS.

Also, a plurality of effluent solutions from the high speed liquid chromatography and a plurality of kinds of additive constituents may be mixed.

In this invention, since the probe has the mixture flow passage for mixing an additive constituent other than the effluent solution into the effluent solution and the gas exhaust nozzle for blowing a gas to expel a liquid to be desorbed from the distal end, an appropriate amount of liquid can be dropped by blowing the gas to eliminate the liquid droplet sticking to the distal end of the probe, in dropping the liquid from the distal end, thereby allowing the fine adjustment for the drop amount of liquid. Also, it is unnecessary to wait until the effluent solution sticks or drops onto the object spot.

Since the distal end of the probe may have a multi-pipe structure, in which the effluent solution passes through a central flow passage, the additive constituent passes through an outer flow passage, and the gas passes through an outermost flow passage, it is possible to increase the effect of dropping the liquid droplet due to blowout of the gas, and perform the division and collection more efficiently. Furthermore, employing the structure in which the distal end of the outermost pipe extends beyond the distal end of the inner pipes, a space for gathering the liquid is provided at the distal end portion of the probe.

If the outermost surface of the probe is coated with a hydrophobic substance, it is possible to prevent the liquid droplet from being swollen at the distal end of the probe to reach the distal end of the probe, when dropped, and the effluent solution from being contaminated, even though the effluent solution contains a constituent having a large surface tension.

If the additive constituent flowing through the flow passage of the probe is a matrix solution for MALDI-TOF-MS, the fractionating apparatus is dedicated for MALDI-TOF-MS.

Also, if a plurality of effluent solutions from the high speed liquid chromatography and a plurality of kinds of additive constituents are mixed, a post column reaction in the typical high speed liquid chromatography is performed in micro scale.

DETAILED DESCRIPTION OF THE INVENTION

Figure 1:
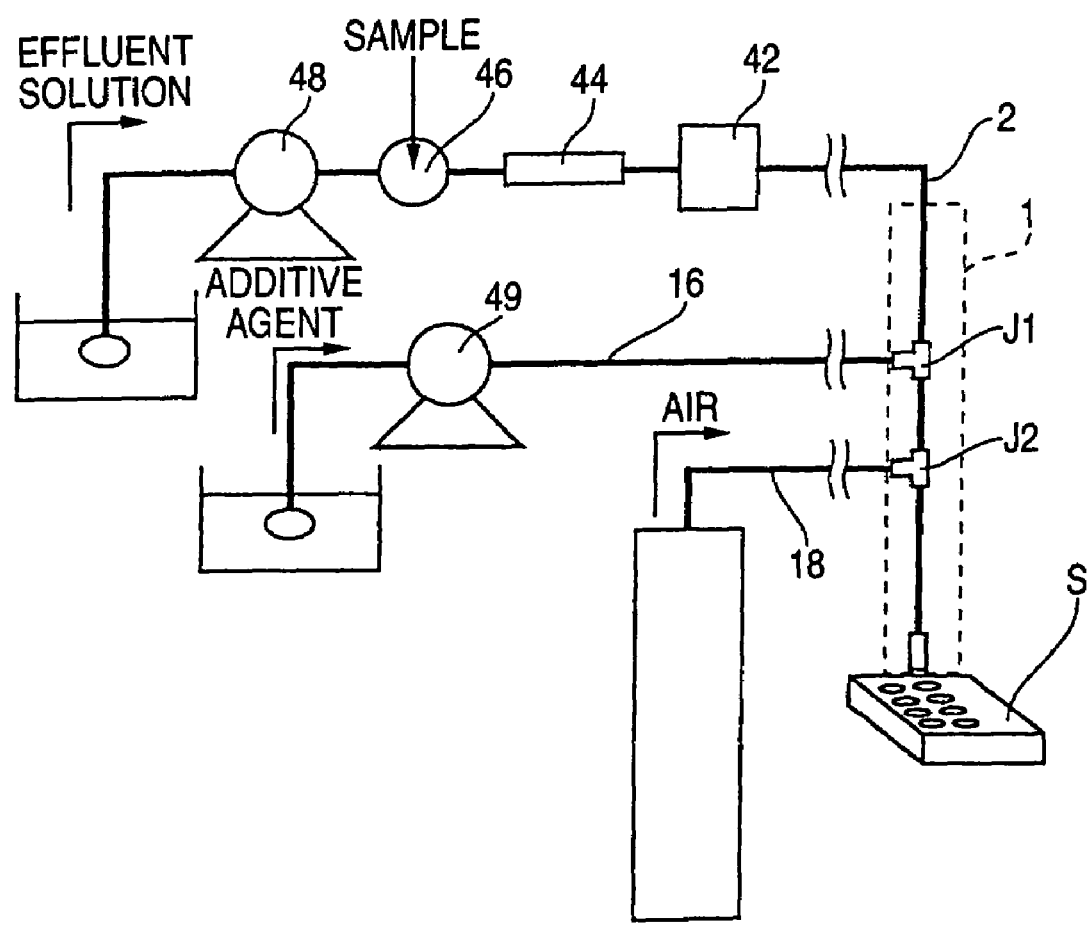
FIG. 1 is a schematic diagram showing a fractionating apparatus for liquid chromatography according to one embodiment of the present invention.

FIG. 1 is a schematic diagram showing a fractionating apparatus for liquid chromatography according to one embodiment of the present invention.

A fractionating apparatus for micro liquid chromatography comprises a pump 48 for feeding an effluent solution, an injector 46 for injecting a sample, a column 44 for separating the sample constituents, and a detector 42, which are disposed along a flow passage of the effluent solution. A probe 1 for dropping a liquid droplet is connected via a capillary 2 on the downstream side of the detector 42.

The probe 1 has the T-type three-way joints J1 and J2, in which an upstream joint J1 connects a capillary 2 for feeding the effluent solution and a pipe 16 for feeding an additive agent such as matrix solution, and a downstream joint J2 connects a pipe 18 for supplying the air. A distal end portion of the probe 1 on the exit side forms a triple pipe structure.

The effluent solution is fed by the pump 48, and the sample is injected from the injector 46. The sample injected from the injector 46 is separated into constituents in the column 44, the constituents being detected by the detector 42. The effluent solution passing through the capillary 2 is dropped from the probe 1 onto a sample container S and collected.

The additive agent such as matrix solution is fed through the pipe 16 connected with the capillary 2 at the T-type three-way joint J1 by the pump 48 to flow outside the capillary 2 and mixed with the effluent solution at the distal end portion of the probe 1.

The air supply pipe 18 is connected with the capillary 2 through which the effluent solution flows and the pipe through which the additive agent flows by the T-type three-way joint J2, in which the air flows outside the pipe through which the additive agent flows and is blown out in dropping the liquid droplet from the distal end of the probe 1 to expel the liquid sticking like liquid droplet to the distal end of the probe 1 on the exit side to be desorbed.

The probe 1 that is a feature of the invention will be described in detail.

Figure 2A:
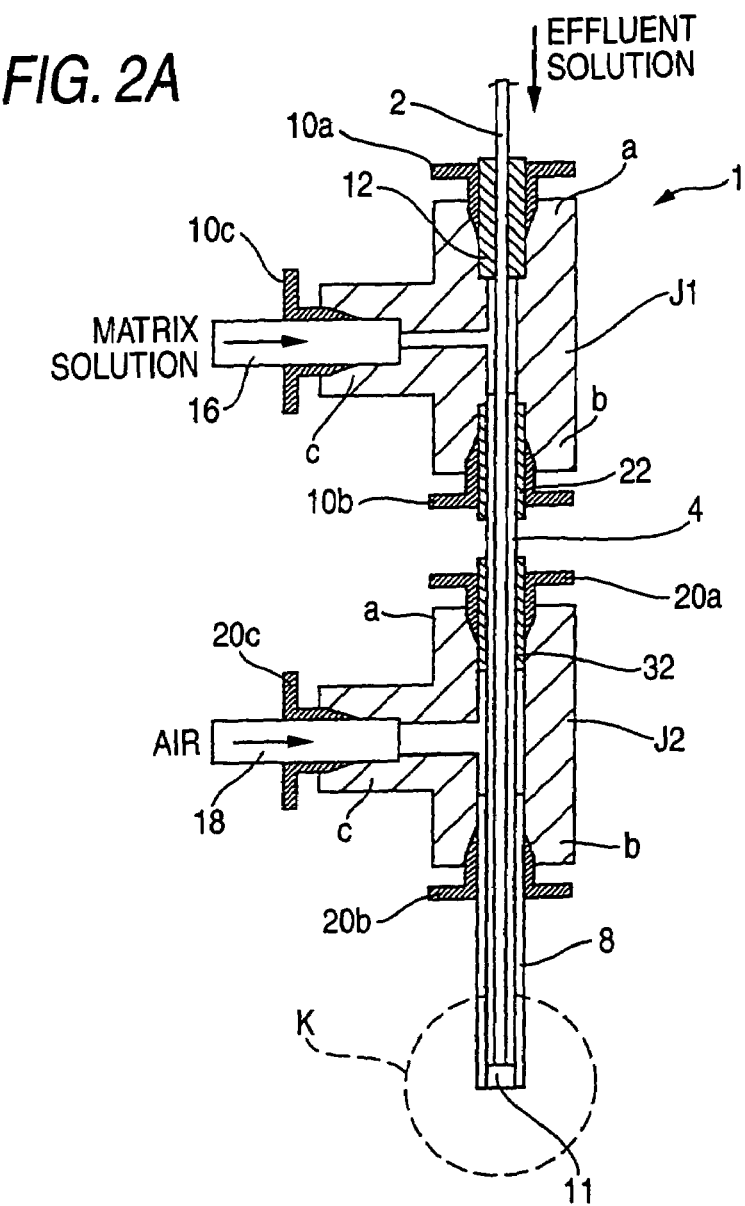
FIG. 2A is a cross-sectional view of a probe according to the embodiment of the invention.
Figure 2B:
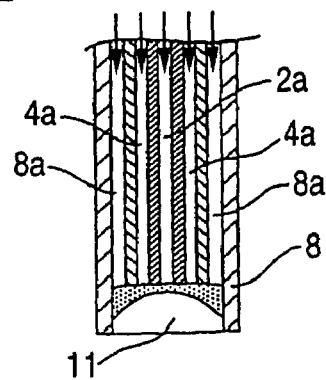
FIG. 2B is an enlarged view of an exit portion K of the probe.

FIGS. 2A and 2B are views showing the structure of the probe 1, in which FIG. 2A is a cross-sectional view of the probe 1, and FIG. 2B is an enlarged view of the exit portion K.

As shown in FIG. 2A, two joints a and b, which are not orthogonal to each other, in a first T-type three-way joint J1 on the upstream side, are crossed by the slenderest capillary 2 through which the effluent solution from the high speed liquid chromatography is fed. The capillary 2 is the fused quartz capillary having an inner diameter of 50 μm and an outer diameter of 150 μm, for example. The upstream joint a is sealed with a pipe fitting 10a such as a male nut, but may employ a sleeve 12, as needed.

An orthogonal joint c of the T-type three-way joint J1 is connected with the pipe 16 through which an additive agent such as matrix solution is fed, and sealed with a pipe fitting 10c such as a male nut. A joint b from which the slenderest capillary 2 extends is covered with a fused quartz capillary 4 having an inner diameter 200 μm and an outer diameter of 370 μm, for example, and sealed with a pipe fitting 10b such as a male nut, but may employ a sleeve 22, as needed.

The capillaries 2 and 4 are inserted from the upstream joint a into the downstream T-type three-way joint J2, and sealed with a pipe fitting 20a such as a male nut, but may employ a sleeve 32, as needed. A joint c orthogonal to the capillaries 2, 4 is connected with the pipe 18 through which the air is supplied, and sealed with a pipe fitting 20c such as a male nut. A joint b on the most downstream side is covered with a stainless pipe 8 having an inner diameter 500 μm and an outer diameter of 1600 μm, for example, and sealed with a pipe 20b such as a male nut.

Referring to FIG. 2B, the exit portion K will be described below in detail. FIG. 2B is an enlarged view of the portion encircled by the broken line in FIG. 2A.

The exit portion of the probe 1 according to this embodiment has a triple pipe structure, in which the effluent solution from the high speed liquid chromatography flows through an innermost flow passage 2a, the matrix solution flows through a flow passage 4a outside it, and the air flows through an outermost flow passage 8a.

The distal end of the outermost piping 8 extends 1 or 2 mm longer than the distal end of the duplex tube inside it to form a liquid reservoir 11. The liquid gathered in this liquid reservoir 11 is a mixture solution of the effluent solution from the high speed liquid chromatography and the matrix solution. When this mixture solution is at an appropriate amount, the air is blown out from a flow passage 14 to drop the mixture solution while adjusting the amount of liquid. Since the distal end of the outermost piping 8 extends beyond the distal end of the inner pipes, the blowout of air does not occur circumferentially at the distal end of the probe, but is stronger in the inner direction, thereby enhancing the effect of dropping the liquid droplet to make the division and collection more efficiently.

Usually, the feed flow rate of the high speed liquid chromatography is 1 μL/min. Hence, the liquid is fed at the same feed flow rate of 1 μL/min as in the micro high speed liquid chromatography by adjusting the concentration of matrix solution. Accordingly, a mixture solution 12 is gathered at a rate of 2 μL/min in the liquid reservoir 11 at the distal end of the probe 1 on the exit side.

When the inner diameter of the outermost piping 8 is 500 μm, the capacity of the liquid reservoir 11 is 200 nL, if the length of a portion of the outermost piping 8 extending from the inner duplex tube is 1 mm. Accordingly, since the mixture liquid of 200 nL is gathered in six seconds in the liquid reservoir 11, the air is blown out at every six seconds to extrude the constituents reserved in the liquid reservoir 11. At this time, the extruding amount and speed of air are controlled so that the liquid droplet may be dropped reproducibly.

Usually, if the mixture solution continues to be fed without blowing out the gas such as air, the liquid droplet is formed at the distal end of the probe. When the constituent of the mixture solution has a large surface tension, like water, the capacity is about 5 μL. Accordingly, when the liquid droplet is dropped without blowing out the gas such as air, the size of liquid droplet is about 5 μL at minimum, which is disadvantageous for the MALDI-TOF-MS analysis. In the case of making a gradient analysis with the micro high speed liquid chromatography, the effluent solution is changed into a state with higher concentration of an organic solvent, and due to a small surface tension of the organic solvent, the liquid droplet is smaller with the elapse of time, whereby the uniform drop amount is not expected.

Also, it is preferred that the outside surface of the outermost piping 8 is coated with Teflon (registered trademark) having hydrophobic property. Therefore, the mixture solution may overflow from the distal end to form a liquid bubble at the distal end of the probe, but the liquid does not reach the outside surface of the outermost piping 8, thereby preventing cross contamination of the fractionated constituents.

A PEEK (polyether-ether-ketone) tube may be employed instead of the stainless piping 8.

Figure 3:
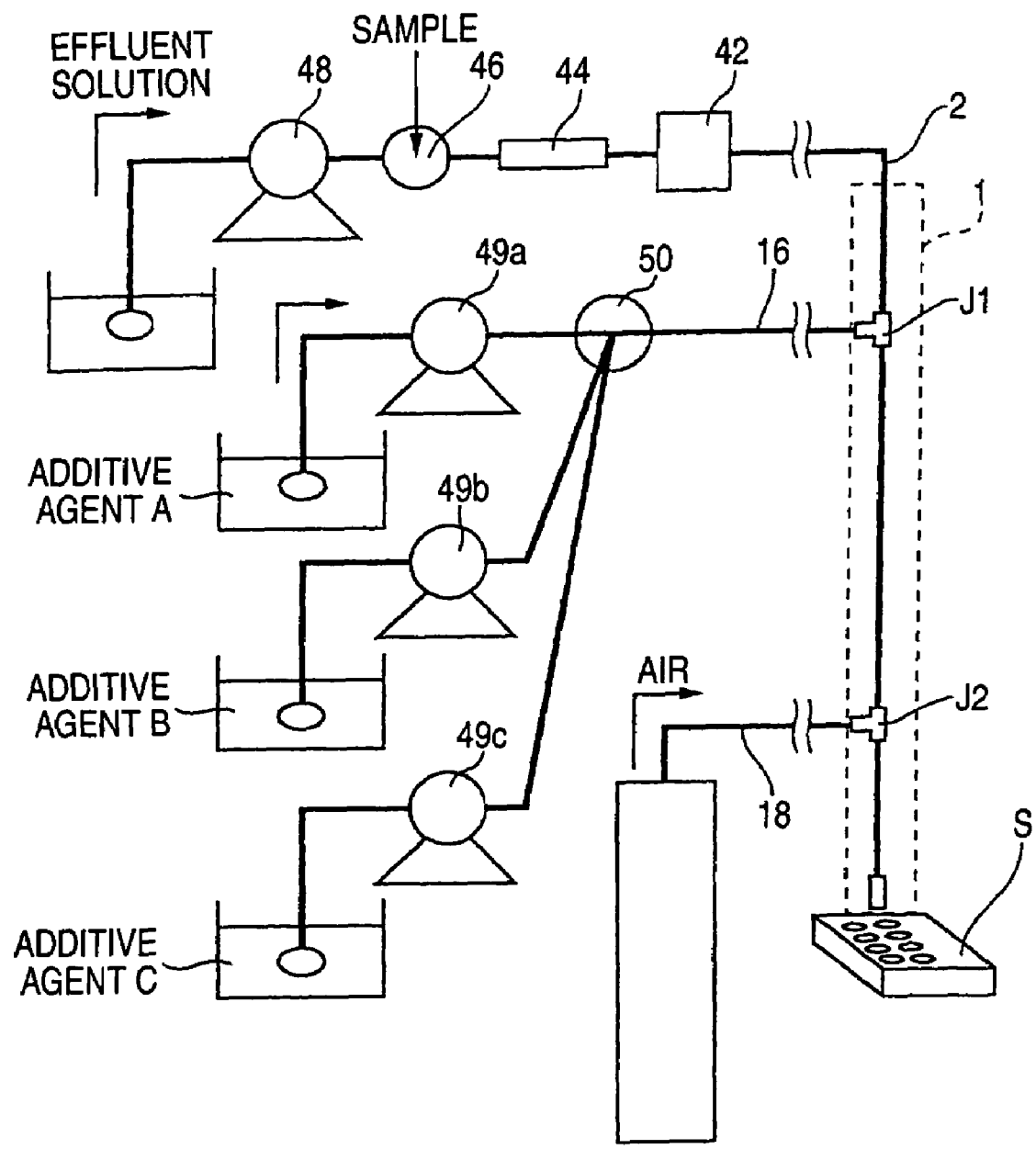
FIG. 3 is a schematic diagram showing a fractionating apparatus for liquid chromatography according to another embodiment of the invention.

FIG. 3 shows a second embodiment in which a plurality of additive agents are added, instead of the matrix solution.

In the embodiment of FIG. 1, the flow passage for supplying the additive agent such as matrix solution is connected via the three-way joint J1. However, in the second embodiment of FIG. 3, the flow passages for supplying a plurality of additive agents A to C are connected via the three-way joint J1. The additive agents A to C are fed by the liquid feed pumps 49*a* to 49*c*, joined via a joint 50, passed through the pipe 16 connected with the capillary 2, flowed outside the capillary 2, and mixed with the effluent solution at the distal end of the probe 1.

With this embodiment, a post column reaction as seen in the typical high speed liquid chromatography can be effected in micro scale.

The fractionating apparatus of this invention may be utilized as the apparatus for making the post column analysis to prepare the effluent solution from the high speed liquid chromatography for the sample for MALDI-TOF-MS analysis, or the sample for subsequent analysis.

What is claimed is:

1. A fractionating apparatus for fractionating an effluent solution fed from a liquid chromatography, the apparatus comprising: a probe having a distal end and a micro plate or a sample plate positioned beneath the probe, the probe having a mixture flow passage for mixing the effluent solution from the liquid chromatography and an additive constituent other than the effluent solution into the effluent solution, and a gas exhaust nozzle in communication with the mixture flow passage for blowing a gas in predetermined intervals to expel the mixture of the effluent solution and the additive as a liquid droplet from the distal end of the probe onto the micro plate or sample plate.

2. The fractionating apparatus according to claim 1, wherein said probe has a multi-pipe structure at its distal end portion, the multi-pipe structure having a central flow passage, an outer flow passage and an outermost flow passage, wherein the effluent solution passes through the central flow passage, the additive constituent passes through the outer flow passage, and the gas passes through the outermost flow passage, and wherein a distal end of an outermost pipe extends beyond a distal end of inner pipes.

3. The fractionating apparatus according to claim 2, wherein an outermost surface of said probe is coated with a hydrophobic substance.

4. The fractionating apparatus according to claim 1, wherein an outermost surface of said probe is coated with a hydrophobic substance.

5. The fractionating apparatus according to claim 1, wherein said additive constituent is a matrix solution for MALDI-TOF-MS.

6. The fractionating apparatus according to claim 1, wherein a plurality of effluent solutions from a high speed liquid chromatography and a plurality of kinds of additive constituents are mixed at a distal end portion on an exit side of said probe.

* * * * *